(12) United States Patent
Schläpfer et al.

(10) Patent No.: US 8,012,184 B2
(45) Date of Patent: Sep. 6, 2011

(54) DEVICE FOR STABILIZING BONES

(75) Inventors: Fridolin Schläpfer, Hoelstein (CH); Martin Hess, Hölstein (CH)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 12/580,167

(22) Filed: Oct. 15, 2009

(65) Prior Publication Data

US 2010/0036428 A1 Feb. 11, 2010

Related U.S. Application Data

(60) Division of application No. 11/147,136, filed on Jun. 6, 2005, now Pat. No. 7,621,941, which is a continuation of application No. PCT/CH02/00672, filed on Dec. 6, 2002.

(51) Int. Cl.
*A61B 17/70* (2006.01)
(52) U.S. Cl. ...................................................... 606/264
(58) Field of Classification Search .................. 606/264, 606/267, 305
See application file for complete search history.

(56) References Cited

U.S. PATENT DOCUMENTS

| 5,501,684 | A | * | 3/1996 | Schlapfer et al. ............ 606/301 |
| 6,030,389 | A | * | 2/2000 | Wagner et al. .................. 606/71 |
| 6,273,914 | B1 | | 8/2001 | Papas | |
| 6,290,703 | B1 | | 9/2001 | Ganem ......................... 606/250 |
| 6,626,904 | B1 | * | 9/2003 | Jammet et al. ................ 606/266 |

FOREIGN PATENT DOCUMENTS

| DE | 4040368 | 8/1991 |
| FR | 2715057 | 7/1995 |
| TW | 297760 | 9/2006 |

OTHER PUBLICATIONS

International Search Report dated Aug. 5, 2003.

* cited by examiner

*Primary Examiner* — Eduardo C Robert
*Assistant Examiner* — Elana Fisher
(74) *Attorney, Agent, or Firm* — Stroock & Stroock & Lavan, LLP

(57) ABSTRACT

A device pivotally connects two stabilizing parts to a bone. The device comprises at least one bone fixing element with a central axis, an anchor part designed to be fixed in or onto the bone, and a head part that can be attached to both stabilizing parts. The two stabilizing parts are located axially one below the other. Each stabilizing part has a cavity there through running coaxially to the central axis. A clamping element, which can be elastically deformed transversely to the central axis, is rotatably mounted in each cavity. The clamping element has a central bore running coaxially to the central axis for receiving the head part. The device comprises at least one wedge or cone that can be axially clamped in the central bores, enabling the head part of the bone fixing element to be removably fixed in at least one of the stabilizing parts.

10 Claims, 6 Drawing Sheets

DEVICE FOR STABILIZING BONES

CROSS-REFERENCE TO RELATED APPLICATIONS

This application is a divisional application of U.S. patent application Ser. No. 11/147,136, filed on Jun. 6, 2005 entitled "Device For Stabilizing Bones", now U.S. Pat. No. 7,621,941, which is a continuation of International Patent Application No. PCT/CH2002/000672, filed Dec. 6, 2002, the entire contents of which are incorporated herein by reference thereto.

BACKGROUND OF THE INVENTION

The invention relates to a device for pivotally connecting two stabilization parts belonging to a fixing device for bones to a bone-fixing element.

An osteosynthetic fixing device for connecting a fixing element, such as a pedicle screw with a longitudinal member, is known. This known fixing device is suitable as a plate/screw system, as an external or internal fixator, and particularly for fixing a spinal column. It has an articulated connection between the fixing element and the longitudinal member, comprising a connecting element with a completely open, spherically configured cavity and an elastically expandable clamping element with a spherical outer wall with a complementary, spherically configured cavity. The fixing element has a conical element abutting the anchoring segment in the bones that can be screwed into the bone. The conical segment can be wedged into an inner cone in the clamping element, whereby the clamping element is radially expanded and secured in the cavity. The mounting device for the longitudinal member in the connecting element is realized by a borehole, with its axis running transversely to the central axis of the fixing element. Such a device, however, permits only the connection of two objects. If three or more have to be connected, the system fails.

Therefore, it is an object of the invention to create a connection between a bone-fixing element and two longitudinal members, whereby the angles of the two members can be adjusted individually and attached to the bone-fixing element. This makes it possible to build on a multi-segmental fixation system sequentially, from one object to the other.

BRIEF SUMMARY OF THE INVENTION

Pursuant to the invention, this objective is accomplished with a device for a pivotable connection between two stabilizing parts of a fixing device for bones and a bone-fixing element.

The advantages of the invention allow two stabilizing parts, for example, to be connected pivotably and independently of one another relative to a bone fixation element, such as a pedicle screw or a pedicle hook. An expensive pre-bending of the longitudinal members is thus avoided.

In a preferred embodiment, the device also comprises a tensioning element, which engages the head part of the bone fixation element for the axial displacement of at least one wedge or cone.

In other preferred embodiments, the device comprises the following distinguishing features:
  at least one wedge or cone that forms a single unit with the head part of the bone-fixing element, and/or
  at least one wedge or cone that forms a single unit with the tensioning element.

In yet another embodiment, the device comprises an upper and a lower wedge or cone, the lower wedge or cone expanding toward the anchoring element at the bone-fixing element and the upper wedge or cone expanding toward the rear end of the bone-fixing element.

In another embodiment with two wedges or cones, the following configurations, for example, are possible:
  the upper wedge or cone forms a single unit with the clamping device; and/or
  the lower wedge or cone forms a single unit with the head part of the bone-fixing element.

In another embodiment, the bone-fixing elements are configured in such a way that their head part, at the end, comprises a bolt with an external thread that is coaxial with the central axis. The clamping elements preferably comprise a nut, which can be screwed over the external thread onto the head part of the bone-fixing element.

In yet another embodiment, the bone-fixing elements are configured in such a way that their head part at the rear end has a borehole with an internal thread that is coaxial to the central axis. Here, the clamping elements preferably include a screw with an internal thread.

In another embodiment of the inventive device, the cavities in the stabilizing parts are spherical and the outer walls of the clamping element are spherically complementary thereto.

In another embodiment of the inventive device, the outer walls of the clamping elements are configured spherically, whereas the cavities in the stabilizing parts have a central cavity, enlarged in relation to the clamping elements, with two terminal constrictions. The constrictions terminally have circular edges, which are concentric with the central axis and against which the clamping elements rest. A linear contact can be established between the clamping elements and the cavities by means of this configuration of the cavities.

In yet another embodiment of the inventive device, the cavities are spherical whereas the outer walls of the clamping element are configured with circular cylindrical segments that are arranged axially one behind the other. In addition, a linear contact can be established between the clamping elements and the cavities also by this configuration of the clamping elements.

In a further embodiment, the clamping element, disposed in the lower stabilizing part, can be fixed by the first clamping element in the cavity of the lower stabilizing part, and the clamping element, arranged in the upper stabilizing part, can be fixed by the second clamping device in the cavity of the upper stabilizing part. It is thus possible to achieve the advantage that the two stabilizing parts can be attached, independently of one another, to the head part of the bone-fixing device. Preferably, the head part comprises two cones separated by a threaded spacer, the threaded spacer being positioned axially with respect to the clamping element in such a manner that the clamping element can be blocked by a tensioning device that can be mounted on the threaded spacer.

In another embodiment, a tensioning device comprises a threaded part and a cone, which adjoins axially, expands toward the threaded part and is configured complementary to the internal cone in one of the clamping elements. Further, the clamping element projects axially beyond the head part and, at the rear end of the bone fixing device, the head part has a borehole with an internal thread, so that the threaded part can be screwed into this internal thread. The cone of the tensioning device preferably ends at a threaded bolt, which protrudes axially beyond the clamping element and onto which the second tensioning device, which is provided with an internal thread, can be screwed.

Conversely, the first tensioning device can be configured in such a way that the tapered end of the cone has a borehole with an internal thread, into which a second tensioning device, having an external thread and a head, can be screwed.

Other embodiments are distinguished in that:
the outer surfaces of the clamping elements are roughened;
the surfaces of the cavities are roughened;
the outer surfaces of the clamping element comprise a three-dimensional structuring;
the surfaces of the cavities comprise a three-dimensional structuring; and/or
at least one clamping element includes a material that is softer than the material of the wall of the corresponding cavity.

BRIEF DESCRIPTION OF THE SEVERAL VIEWS OF THE DRAWINGS

The invention is explained in greater detail by means of the partially diagrammatic representations of several examples.

In the drawings.

DETAILED DESCRIPTION OF THE INVENTION

Figure 1:
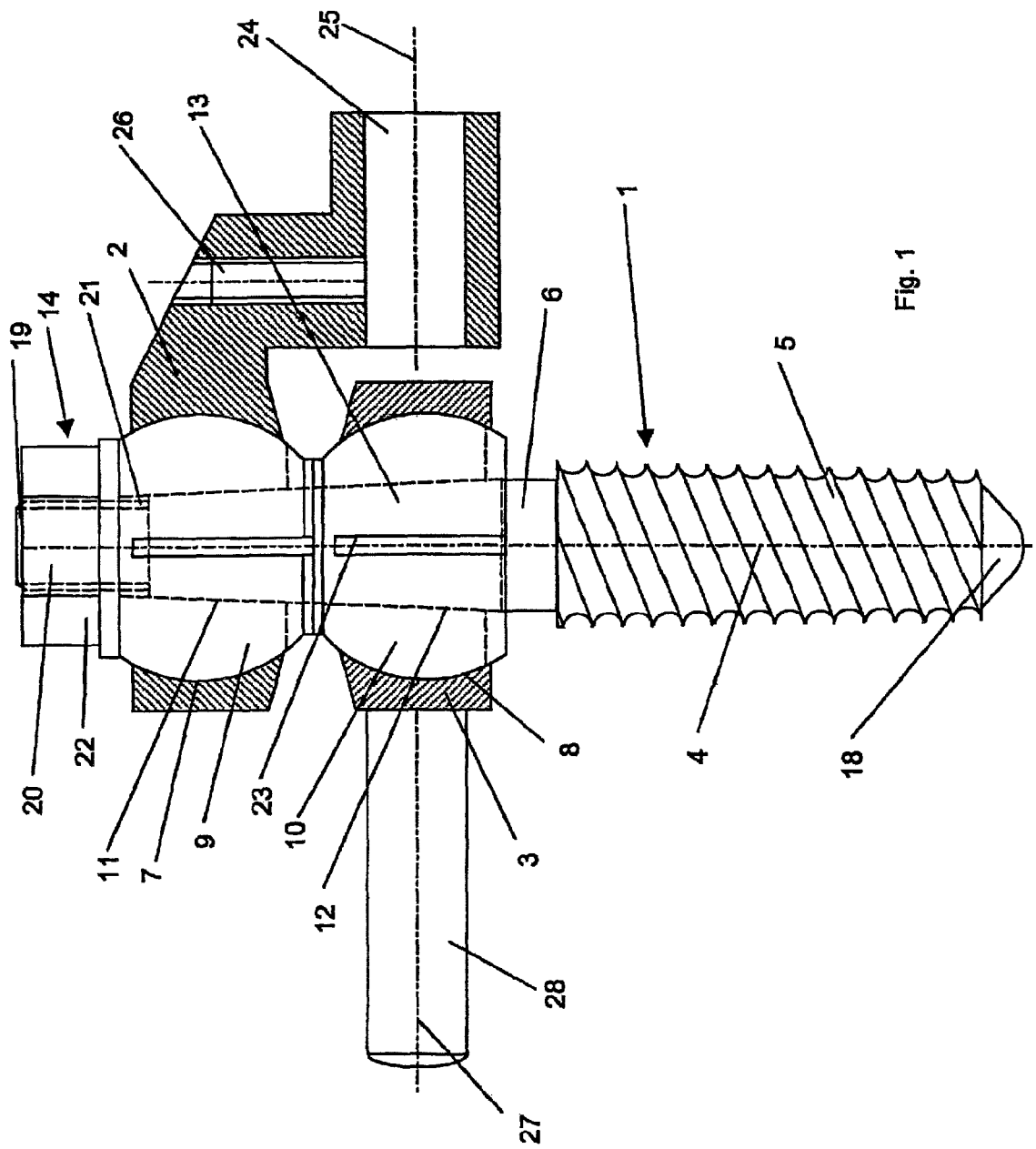
FIG. 1 shows an embodiment of the inventive device with a cone, which is formed in one piece with the bone-fixing element.

FIG. 1 shows an embodiment of the inventive device with a bone-fixing element 1 configured as a pedicle screw, an upper stabilizing part 2 and a lower stabilizing part 3, which could, for example, be parts of a spine fixing device. Both of the stabilizing parts 2,3 have an articulated connection with the head part 6 of the bone-fixing element 1. The anchoring part 5 of the bone-fixing element 1, constructed as a bone screw, can be fixed, for example, in a pedicle. The stabilizing parts 2,3 are arranged axially one behind the other. Each comprises a spherical cavity 7,8 passing through the respective stabilizing part 2,3 coaxially to a central axis 4. A clamping element 9,10, configured externally complementary to the cavity 7,8 and having a central borehole 11,12, is inserted into each of the cavities 7,8. By means of the spherical configuration of the cavities 7,8, as well as that of the clamping elements 9,10, a ball and socket connection between each stabilizing part 2,3 and the clamping element and the bone-fixing element 1 is established. The central boreholes 11,12 penetrate the clamping elements 9,10 coaxially to the central axis 4 and are conically tapered toward the rear end 19 of the bone-fixing element 1 The head part 6 of the bone-anchoring element 1, which comprises a cone 13, which is complementary to both central boreholes 11,12 and tapers toward the rear end 19 of the bone-fixing element 1, is inserted into the central boreholes 11,12. A bolt 20 with an external thread 21, which is also coaxial with the central axis 4, is mounted at the rear end 19 of the bone-fixing element 1. A nut 22, resting at the end of the first stabilizing part 2, can be screwed on over the external thread 21 as a tensioning device 14, so that, when the nut 22 is tightened, the two stabilizing parts 2,3 can be shifted axially on the head part 5 and pressed in the direction of the front end 18 of the bone-fixing element 1. Furthermore, by means of parallel slots 23 parallel to the central axis 4, the clamping elements 9,10 are constructed to be elastically deformable in the radial direction, that is, transversely to the central axis 4. It is thus possible that a bridge effect occurs between the cone 13 and the walls of the central conical boreholes 11,12 when the two conical central boreholes are pushed over the cone 13 at the head part 5 of the bone-fixing element when the nut 22 is tightened. As a result, the two clamping elements 9,10 are expanded transversely to the central axis 4 and the spherical outer walls of the clamping elements 9,10 and the spherical outer walls of the clamping element 9,10 are pressed against the spherical walls of the cavities 7,8. For a connection with another element belonging to the spinal column fixing device, the upper stabilizing part 2 is provided with a depression 24, which is open on the outside at the stabilization part 2 and has a longitudinal axis 25, which is transverse to the central axis 4, so that, for example, a rod-shaped longitudinal member (FIG. 5) can be introduced into the depression 24 and detachably fixed by means of an arresting screw 26, which can be screwed perpendicularly to the longitudinal axis 25 into the upper stabilizing part 2. The lower stabilizing part 3 is provided with a second rod-shaped continuation 28 having a longitudinal axis 27, which is also transverse to the central axis, the continuation 28 and the depression 24 being configured complementary to one another, so that, instead of a longitudinal member, a rod-shaped continuation 28 can also be introduced into the depression 24 of the upper stabilization part 2. The depression 24 and the rod-shaped continuation 28 are arranged on the stabilizing parts 2,3, so that the two longitudinal axes 25,27 are coaxial in the starting position of the device, that is, when the joints have not been rotated.

The embodiment of the inventive device, shown in FIG. 2, differs from the embodiment shown in FIG. 1 in that the cone 13 at head part 6 of the bone-fixing element 1, only passes through the clamping element 10 in the lower stabilizing part 3 and subsequently passes through the bolt 20, which is disposed terminally at the head part 6 of the bone-fixing element 1. Furthermore, the tensioning device 14 is designed as sleeve 29 with a central borehole 30. The internal thread 31, provided in the central borehole 30, can be screwed over the external thread 21 onto bolt 20 and, at the outside, has a second cone 13", which tapers toward the front end 15 of the tensioning device 14. The central boreholes 11,12 in the clamping elements 9,10 are conically complementary, so that the two cones 13',13" taper toward the contacting ends of the clamping elements 9,10. In order to tighten tensioning device 14, devices 32 for accommodating a screwdriver are provided in the central borehole 30 at the rear end 33 of the tensioning device 14 and are constructed here as an hexagonal socket.

Figure 2:
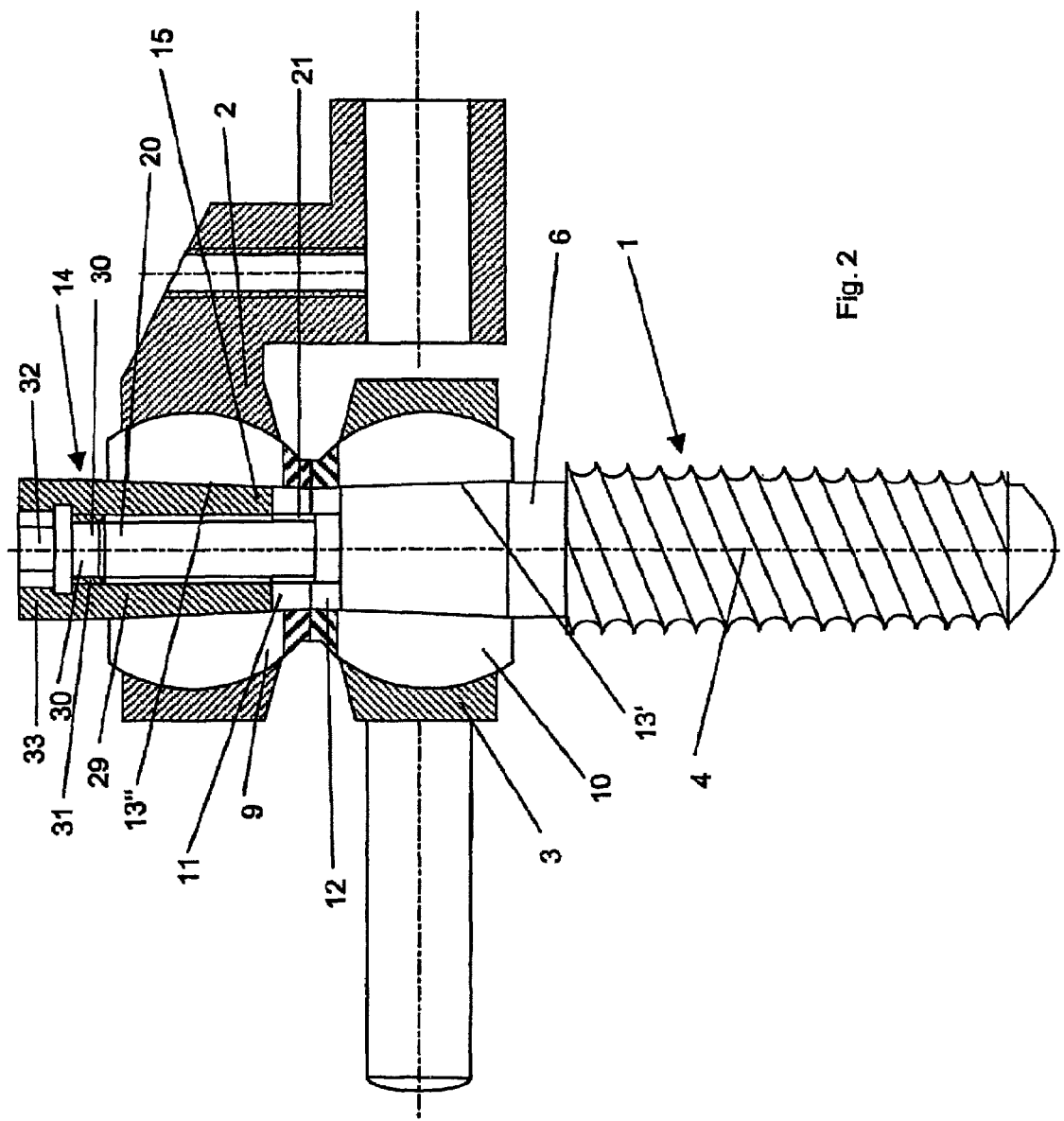
FIG. 2 shows a different embodiment of the inventive device with two cones.
Figure 3:
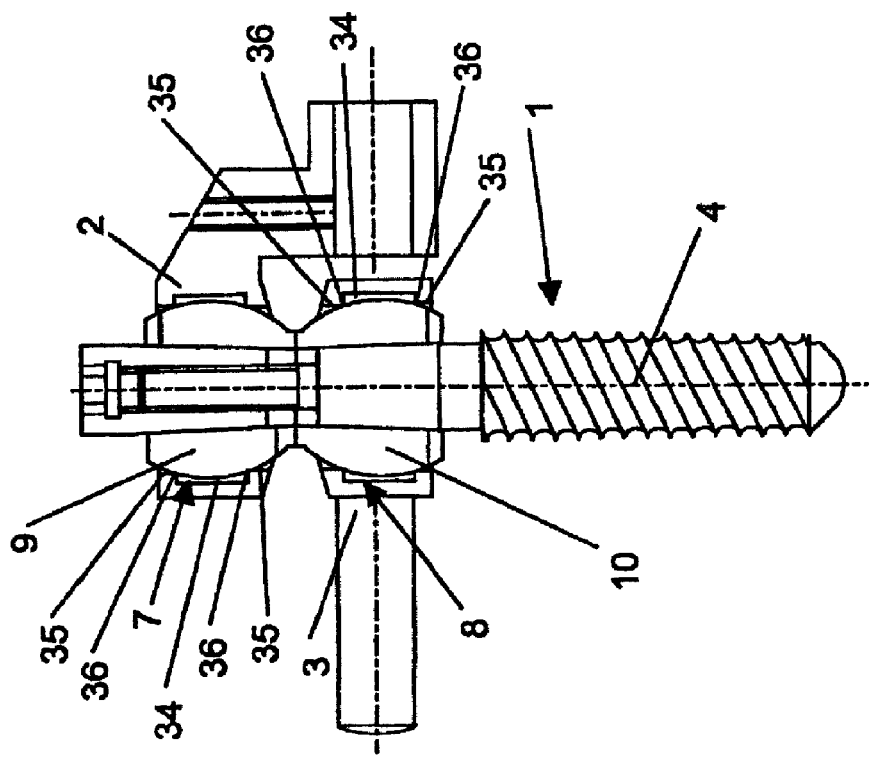
FIG. 3 shows an embodiment of the inventive device, the cavities for accommodating the clamping element including several cylindrical segments.

A further embodiment of the inventive device is shown in FIG. 3. It differs from that shown in FIG. 2 in that the cavities 7,8 in the two stabilizing parts 2,3 are equipped with a central cavity 34, which is larger than the clamping elements 9,10, and with two axial, terminal constrictions 35, the constrictions 35 directed toward cavity 34, each having a circular edge, which is concentric with the central axis 4, so that the spherically constructed clamping elements 9,10 lie against the edges 36, and a linear contact being produced between each cavity 7,8 and the clamping elements 9,10 inserted therein.

Figure 4:
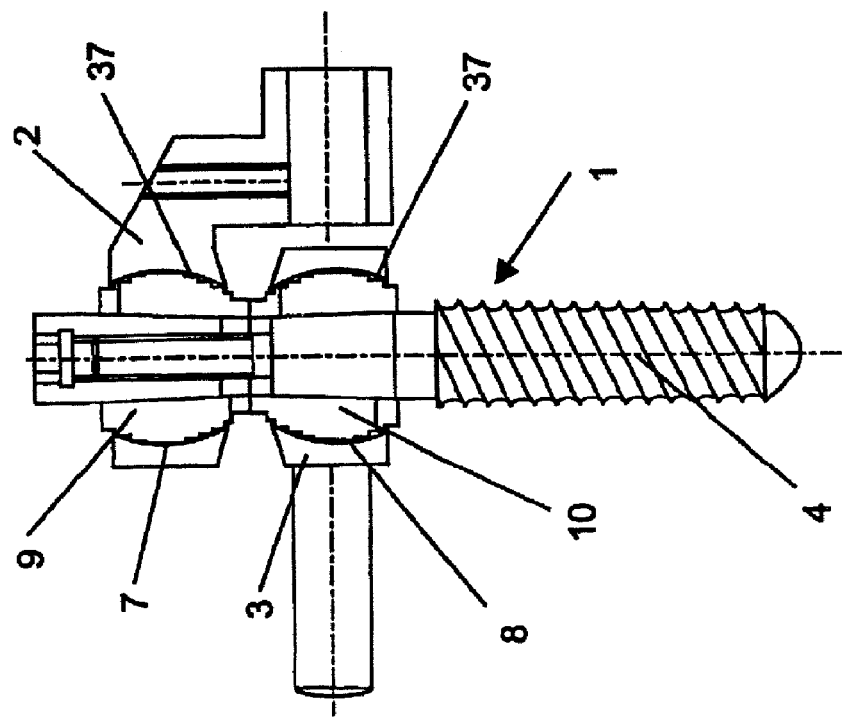
FIG. 4 shows an embodiment of the inventive device, the clamping elements including several axially abutting cylindrical segments.

A further embodiment of the inventive device is shown in FIG. 4, which differs from that shown in FIG. 2 in that the clamping elements 9,10 are externally complementary to the spherical cavities 7,8. Instead, the spherical shape of the cavities 7,8 approach the clamping elements 9,10 is approximated by circular cylindrical segments 17, which are disposed one behind the other axially. Linear contact between the clamping elements 9,10 and the walls of the cavities 7,8 can be produced also with this arrangement.

Figure 5:
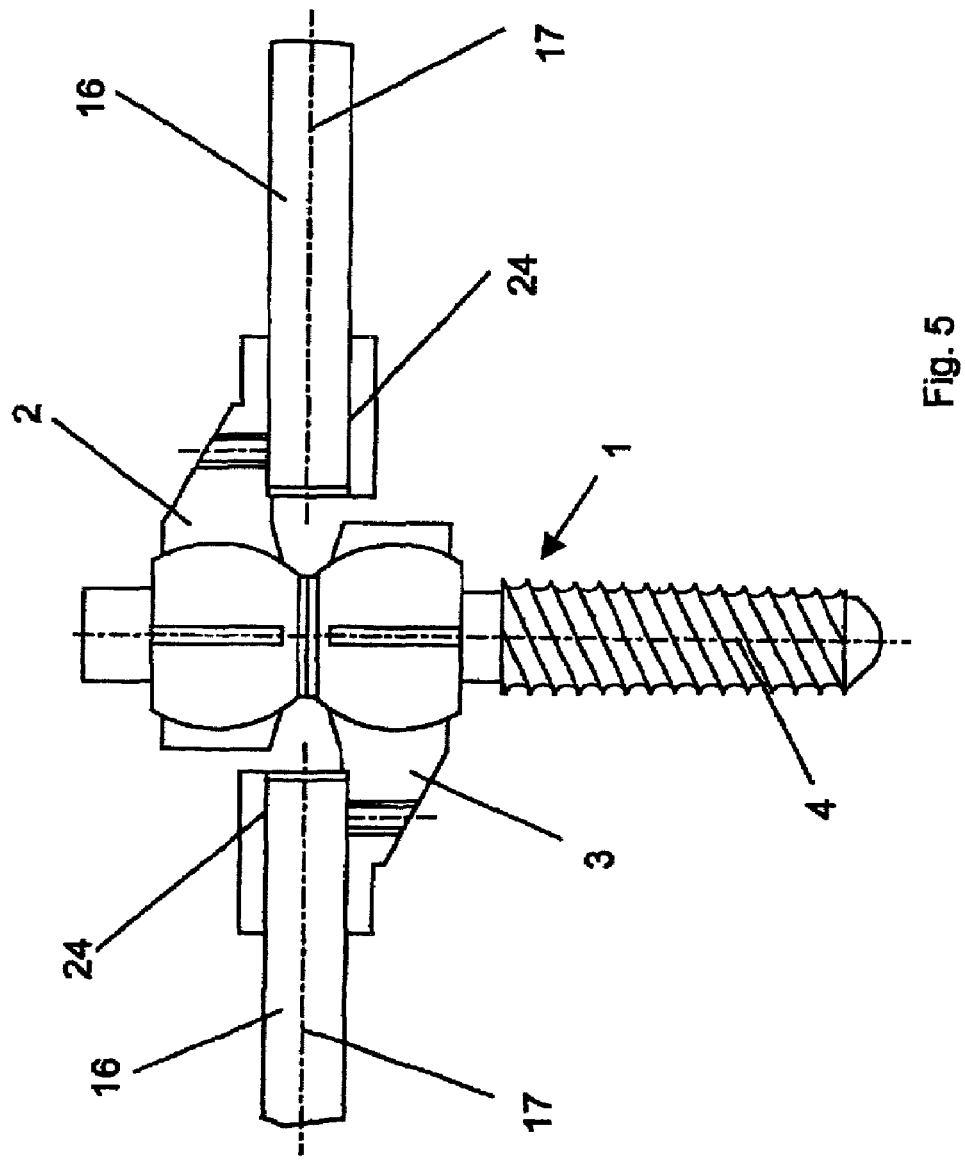
FIG. 5 shows an embodiment of the inventive device, the upper and the lower stabilizing parts comprising bushings for accommodating the longitudinal members.

FIG. 5 shows an embodiment of the inventive device, which differs from that of FIG. 1 in that both stabilizing parts 2,3 have recesses 24 for accommodating for example a longitudinal member 16 each, the longitudinal axes 17 being aligned with one another and disposed perpendicularly to the central axis 4 of the bone-fixing element 1. Furthermore, stabilizing parts 2,3 are constructed so that longitudinal axes 17 of recesses 24 extend approximately at the boundary surface between the two stabilizing parts 2,3.

Figure 6:
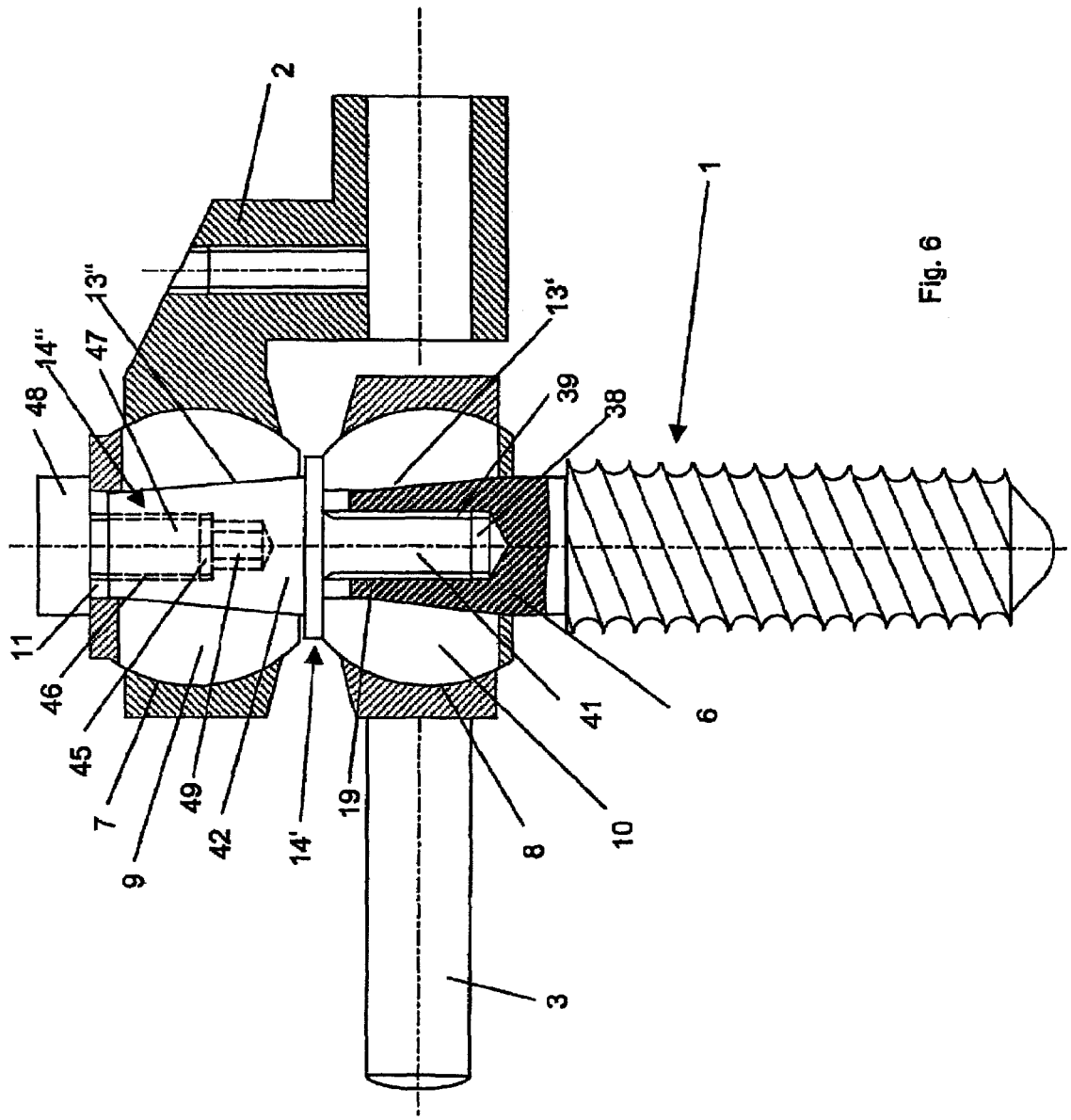
FIG. 6 shows an embodiment of the inventive device, the one-piece cone of the embodiment of FIG. 1 having been divided into two independent cones, with one of the cones serving as the fixing element when connecting the other cone.

FIG. 6 shows an embodiment of the inventive device, which differs from those of FIGS. 1 to 5, in that the clamping element 10, disposed in the lower stabilizing part 3, can be fixed by first tensioning devices 14 in the cavity 8 of the lower stabilizing part 3 and in that the clamping element 9, disposed in the upper stabilizing part 2, can be fixed by the second tensioning devices 14" in the cavity 7 of the upper stabilizing part 2. The clamping element 10 axially protrudes beyond head part 6 of the bone-fixing element 1, the head part 6 having a borehole 38 with an internal thread 39 at the rear end 19 of the bone-fixing element 1. An axially terminal threaded part 41 on the first tensioning device 14 can be screwed into this internal thread 39, so that, when the first tensioning device 14' is tightened by means of screwdriver inserted into the means for accommodating a tool 49, the connection between head part 6 of the bone-fixing element 1 and the lower stabilizing part 3 can be detachably blocked. Furthermore, the first tensioning device 14' comprises a cone 42, which is axially adjacent to the threaded piece 41 at the top, expands toward the threaded piece 41 and can be inserted into the complementary cone 13" in the central borehole 11 in clamping element 9. The clamping element 9 in cavity 7 in the upper stabilizing part 2 extends axially beyond the tapered end of the cone 42 disposed on the first tensioning device 14'. By means of the second tensioning devices 14", which is constructed as a screw and comprises a head 48 contacting the clamping element 9 terminally, as well as an external thread 47, which can be screwed into the borehole 45 having an internal thread 45 and mounted coaxially in the first tensioning device 14', the clamping element 9 can be blocked detachably together with the first tensioning device 14' in the cavity 7 in the upper stabilizing part 2. Instead of being configured as a screw, the second tensioning device 14" may also be configured as a nut and can be screwed over a threaded bolt, which is mounted terminally at the first tensioning device 14'.

Figure 7:
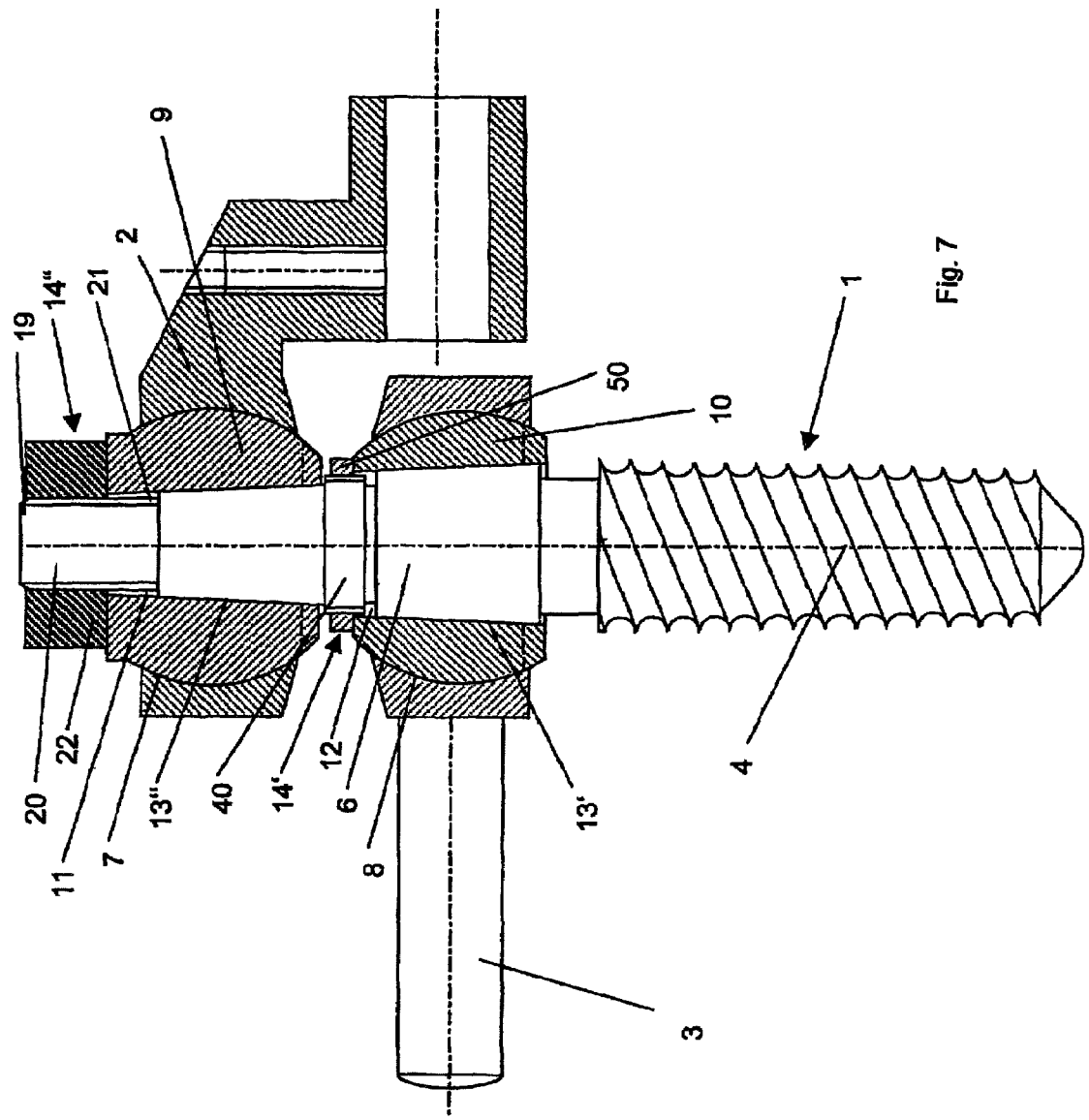
FIG. 7 shows an embodiment of the inventive device, the one-piece cone of the embodiment of FIG. 1 being interrupted by a screw thread, so that the lower cone connection can be fixed independently of the upper cone connection.

The embodiment of FIG. 7 differs from that of FIG. 1 in that the head part 6 of the bone-fixing element 1 comprises two cones 13',13" arranged axially one behind the other. A threaded spacer 40 is disposed between the first cone 13' abutting the anchoring part 5 of the bone-fixing element 1, and the axially terminally disposed second cone 13". Moreover, the first cone 13' is inserted into the central borehole 12 in the clamping element 10, which is constructed conically complementary and serves for fixing the lower stabilizing part 3. The second cone 13" is inserted into the central borehole 11 in the clamping element 9, which is constructed conically complementary and serves for fixing the upper stabilizing part 2. The axial position of the threaded spacer 40 is selected in such a way relative to the clamping element 10, that a first tensioning device 14', constructed as a nut, can be screwed and brought to rest against the end of the clamping element 10 located between the clamping elements 9,10. Accordingly, by tightening the first tensioning device 14', the lower stabilizing part 3 can be blocked detachably independently of the blocking of the upper stabilizing part 3 at the head part 6 of the bone-fixing device 1. Analogously to the embodiment shown in FIG. 1, a bolt 20 with an external thread 21 can be mounted coaxially to the central axis 4 at the rear end 19 of the bone-fixing element 1. A nut 22, resting terminally on the upper stabilizing part 2, can be screwed as second tensioning device 14" over the external thread 21, so that, when the nut 22 is tightened, the upper stabilizing part 2 can be blocked detachably independently of the blocking of the lower stabilizing part 3 at the head part 6 of the bone-fixing device 1.

We claim:

1. A spinal fixation system comprising:
   a bone fixing element having a central axis, an anchoring part for attachment to bone, and a head part;
   a first clamping part having an axial bore for receiving the head part;
   a lower stabilizing part operatively connectable to the first clamping part;
   a first tensioning device operatively connectable to the head part and having an extension extending therefrom;
   a second clamping part having an axial bore for receiving the extension of the first tensioning device;
   an upper stabilizing part operatively connectable to the second clamping part; and
   a second tensioning device operatively associated with the upper stabilizing part,
   wherein the first and second tensioning devices enable independent fixation of the lower and upper stabilizing parts with respect to the bone-fixing element.

2. The spinal fixation system of claim 1, wherein the bone-fixing element is a bone screw.

3. The spinal fixation system of claim 1, further comprising longitudinal spinal rods operatively associated with the lower and upper stabilizing parts.

4. The spinal fixation system of claim 1, wherein the at least one of the lower and upper stabilizing parts is integrally formed as a monolithic unit with one of the longitudinal spinal rods.

5. The spinal fixation of claim 1, wherein the first clamping part has an outer surface that is spherically-shaped and the lower stabilizing part has a spherical cavity for receiving the spherically-shaped portion of the first clamping part, the lower stabilizing part being articulatable relative to the bone fixation element.

6. The spinal fixation of claim 5, wherein the second clamping part has an outer surface that is spherically-shaped and the upper stabilizing part has a spherical cavity for receiving the spherically-shaped portion of the second clamping part, the upper stabilizing part being articulatable relative to the bone fixation element.

7. The spinal fixation system of claim 1, wherein the extension of the first tensioning device is shaped as a tapering cone.

8. The spinal fixation system of claim 1, wherein the second tensioning device is a nut for threadably engaging external threads formed on the extension of the first tensioning device.

9. The spinal fixation device of claim 1, wherein the first tensioning device includes a threaded stem for threadably engaging an internally threaded bore hole formed in the bone fixing element.

10. The spinal fixation device of claim 1, wherein the second tensioning device is a threaded screw for threadably engaging an internally threaded bore formed in the tapered cone.

* * * * *